United States Patent [19]

Hideshima

[11] Patent Number: 5,114,229
[45] Date of Patent: May 19, 1992

[54] APPARATUS FOR MEASURING LEADS OF ELECTRICAL COMPONENT AND METHOD OF MEASURING LEADS OF ELECTRICAL COMPONENT

[75] Inventor: Osamu Hideshima, Tosu, Japan

[73] Assignee: Matsushita Electric Industrial Co., Ltd., Osaka, Japan

[21] Appl. No.: 609,722

[22] Filed: Nov. 6, 1990

[30] Foreign Application Priority Data

Nov. 10, 1989 [JP] Japan .................................. 1-293543

[51] Int. Cl.⁵ ............................................. G01N 21/88
[52] U.S. Cl. ..................................... 356/237; 356/446
[58] Field of Search ............................. 356/237, 446

[56] References Cited

U.S. PATENT DOCUMENTS 4,092,068  5/1978  Lucas et al. ........................... 356/446
4,988,206  1/1991  Melleney et al. ..................... 356/446

Primary Examiner—Vincent P. McGraw
Attorney, Agent, or Firm—Stevens, Davis, Miller & Mosher

[57] ABSTRACT

An apparatus for measuring deviations of positions of leads of an electrical component comprises a light emitting unit for radiating a laser light from below toward the leads projecting from a molding of the electrical component sucked to a nozzle of a pick and place head. First and second photodetectors are disposed at both sides of the light emitting unit for detecting laser lights reflected at the leads, so as to enable to effect the measurement rapidly and accurately.

3 Claims, 3 Drawing Sheets

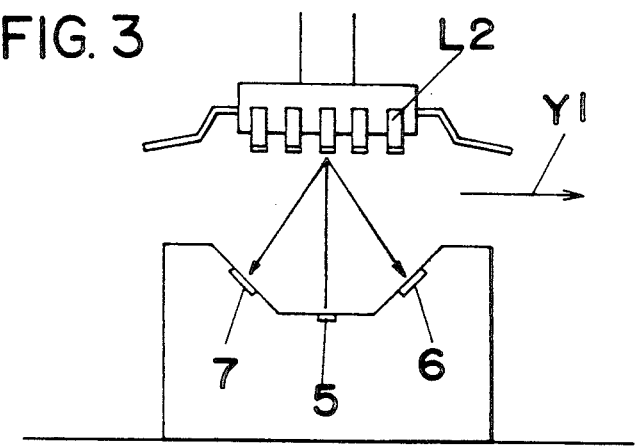
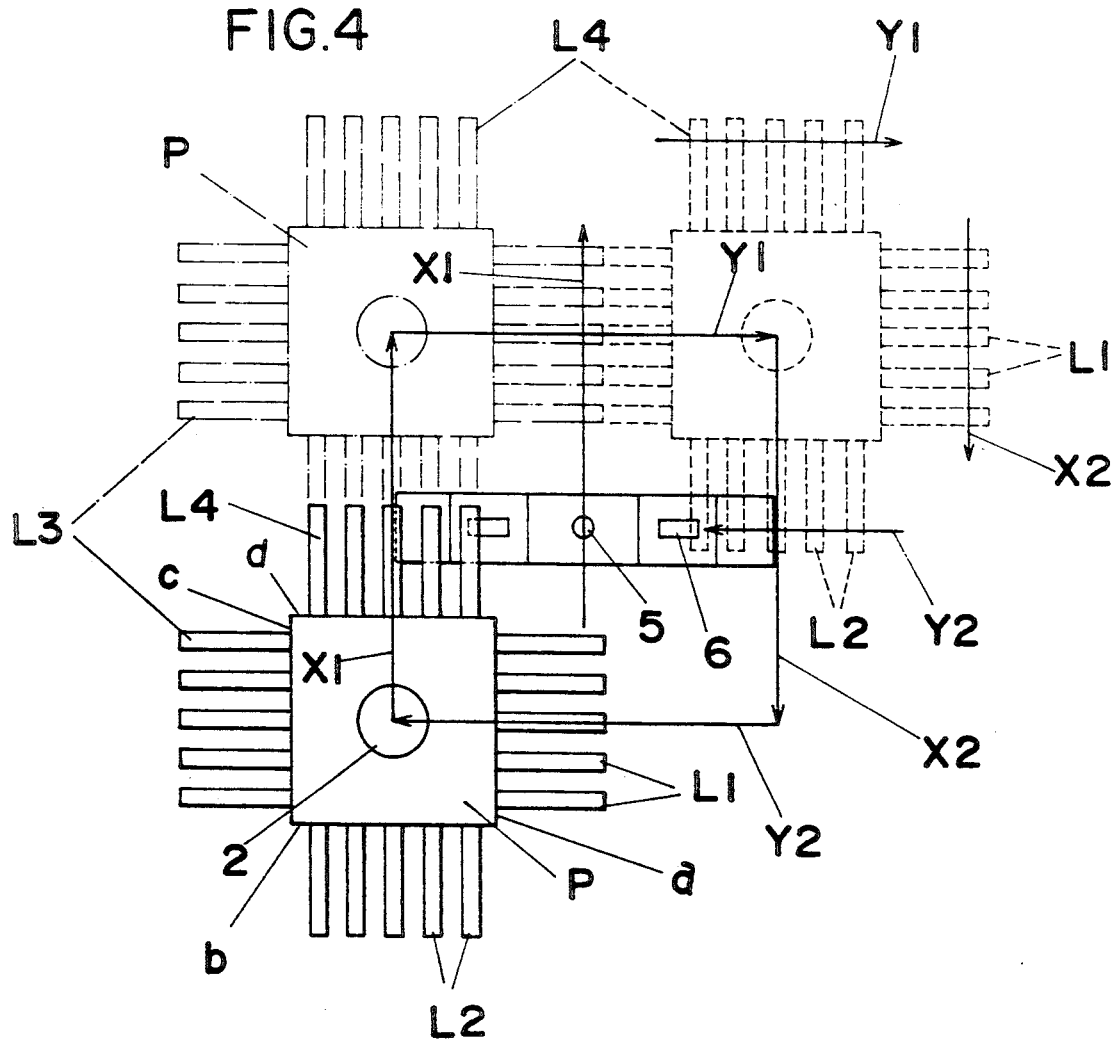

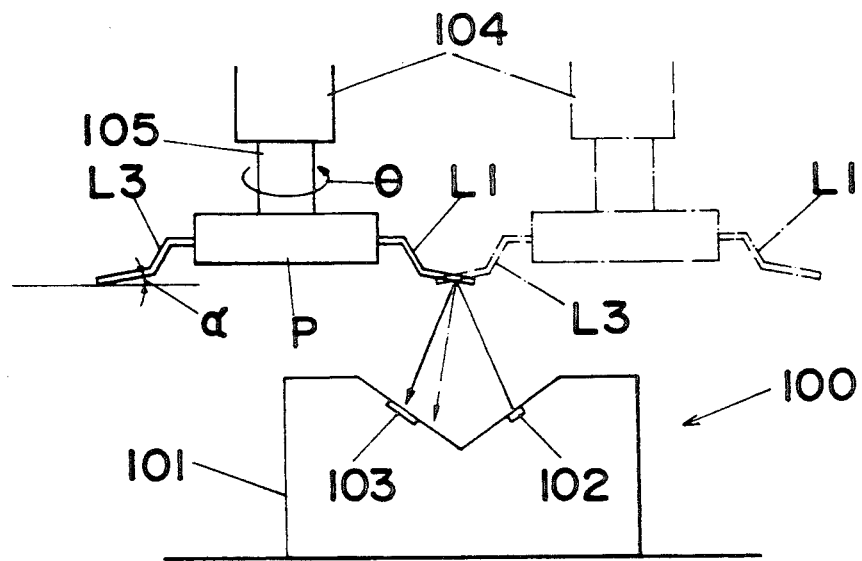
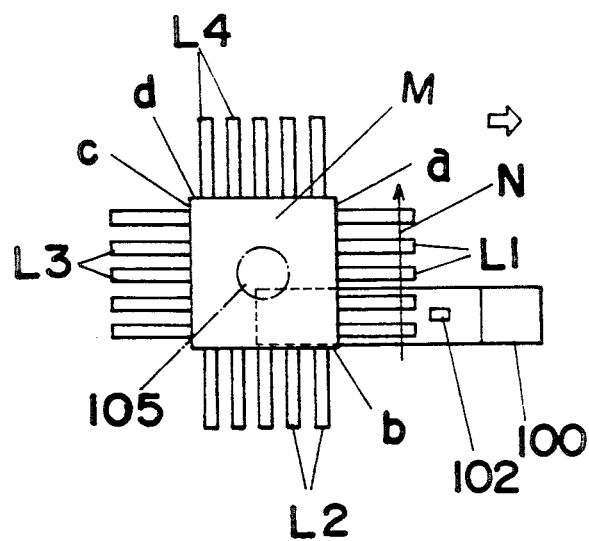 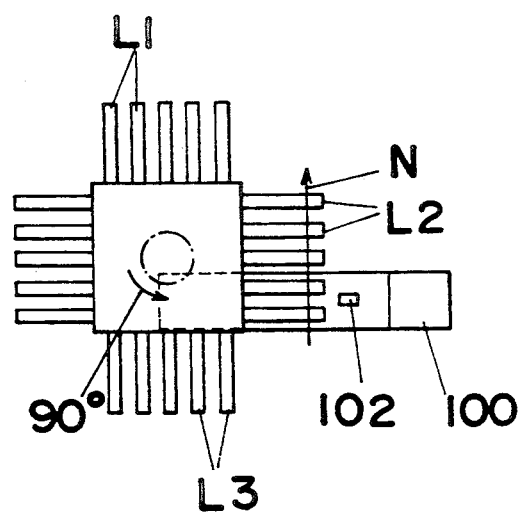

APPARATUS FOR MEASURING LEADS OF ELECTRICAL COMPONENT AND METHOD OF MEASURING LEADS OF ELECTRICAL COMPONENT

BACKGROUND OF THE INVENTION

1. Field of the Invention

This invention relates to an apparatus for measuring leads of an electrical component and a method of measuring leads of an electrical component and, more particularly, to measurements of positional deviations of the leads of the electrical component by providing two photodetectors for detecting laser light reflected from the leads at opposite sides of a light emitting unit.

2. Description of the Prior Art

In order to place an electrical component such as an IC, or an LSI device on a printed circuit board, deviations of the leads of the electrical component in X, Y and Z directions, heights (floating), bends, presence or of the leads, etc., are detected by observing the leads projected from a molding. Heretofore, the leads of the electrical component have been observed by a CCD camera. However, the CCD camera has a small resolution and cannot hence precisely measure extrafine and multiplied leads of the component. Recently, a laser device has been used instead of the CCD camera.

FIG. 5 shows a conventional apparatus 100 for measuring an electrical component with a laser light. A laser light emitting unit 102 and a photodetector 103 are provided on oblique surfaces of a recess formed on a body 101. A laser light is irradiated to be swept from the emitting unit 102 from below towards the leads L of an electrical component sucked to the nozzle 105 of a pick and place head 104, and the laser light reflected from the leads is detected by the photodetector 103 to measure the deviations of positions of the leads L, floating, bends, presence or of the leads L, etc.

However, the ends of the leads L of an electrical component such as a QFP are slightly inclined (at an inclining angle $\alpha$). Accordingly, when the laser light is radiated to be swept at the right side lead L1 to measure the deviation of the position of the lead L1 and the laser light is then irradiated to a left side lead L3 (indicated by dotted broken lines), the reflected laser lights are not, since the directionality of the inclining directions of the leads L1, L3 are different, sufficiently incident to the photodetector 103 as indicated by a dotted broken line with an and the amounts of the reflected lights of the right side lead L1 and the left side lead L3 are irregular, with the result that an error feasibly occurs in the measured values.

As means for eliminating the above-described problem, as shown in FIG. 6(a), it is considered that the pick and place head 104 is first moved in a direction N, a laser light is irradiated to the leads L1 of one side a of a molding M to measure the leads L1, a nozzle 105 is then rotated at 90° as shown in FIG. 6(b), the pick and place head 104 is then similarly moved in the direction N, the laser light is radiated to the leads L2 of the next side b, the laser light is then similarly radiated to the leads L3 and L4 of the other sides c and d to measure the leads L3 and L4.

However, according to this method, since the nozzle 105 must be rotated at 90° at the respective sides to be measured, its operating efficiency is not raised. When the nozzle 105 is rotated at 90°, there arises another problem that the electrical component P might be readily deviated by its centrifugal force. This problem will occur not only at a QFP but an electrical component having bent or inclined leads in many directions such as a PLCC.

SUMMARY OF THE INVENTION

Accordingly, an object of this invention is to provide an apparatus for measuring leads of an electrical component and a method of measuring the leads of an electrical component which can accurately measure the leads of the electrical component with high operating efficiency.

In order to achieve this and other objects according to the present invention, there is provided an apparatus for measuring leads of a electrical component comprising a light emitting unit for radiating a laser light from below toward the leads projected from a molding of the electrical component sucked to a nozzle of a pick and place head, and first and second photodetectors disposed at both sides of said light emitting unit for detecting laser lights reflected at the leads.

With the arrangement described above, the leads projected from one side of the electrical component are disposed over a measuring apparatus, the electrical component is moved in a direction X or Y, a laser light is radiated to be swept at the lead of the side, and the reflected lights are detected by the two photodetectors to measure the leads Then, the electrical component is moved in a direction X or Y as it is without rotating the electrical component, the laser light is radiated to be swept at the leads of next side of the electrical component, the reflected lights are detected by the two photodetectors to measure the leads Similarly, the leads of the other sides are measured.

These and other objects and features of the present invention will become apparent from the following detailed description in conjunction with the attached drawings.

BRIEF DESCRIPTION OF THE DRAWINGS

FIGS. 2 and 3 are front views of the apparatus of FIG. 1;

FIG. 4 is a plan view of the apparatus during measuring;

FIG. 5 is a front view of a conventional apparatus during measuring; and

FIGS. 6(a) and 6(b) are plan views of the apparatus of FIG. 5.

DESCRIPTION OF THE PREFERRED EMBODIMENT

An embodiment of an apparatus for measuring leads of an electrical component according to the present invention will now be described with reference to the accompanying drawings.

Figure 1:
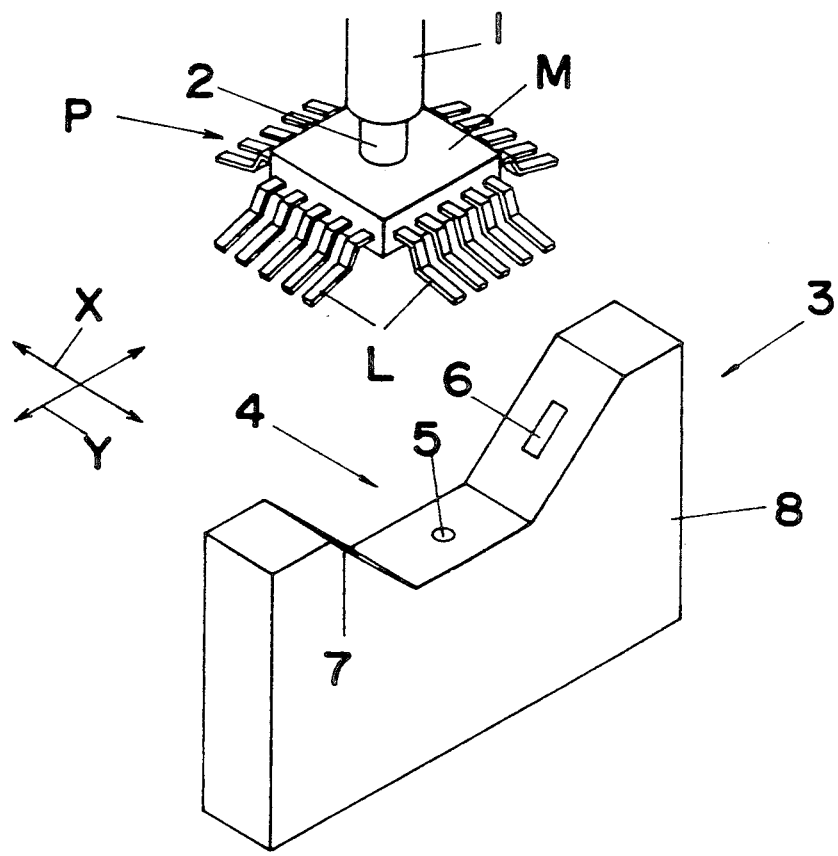
FIG. 1 is a perspective view of an apparatus for measuring leads of an electrical component during measuring according to an embodiment of the present invention.

In FIG. 1, an electrical component P such as a QFP having leads L projected from a molding M in radial four directions is sucked to a nozzle 2 of a pick and place head 1, and placed on a printed circuit board (not shown). A measuring apparatus 3 for measuring leads L of the electrical component P is provided, and a recessed portion 4 is formed on the upper surface of the body 8 of the apparatus 3. A laser light emitting unit 5 is provided on the bottom of the recessed portion 4, and first and second photodetectors 6 and 7 are provided on both side oblique surfaces of the recessed portion 4 at both sides of the laser light emitting unit 5. The laser light emitting unit 5 radiates a laser light from below the leads L toward the leads L. The laser lights reflected downward from the leads L are detected by the first and second photodetectors 6 and 7, and the deviations of the positions of the leads L are measured from the amounts of the received lights.

Figure 2:
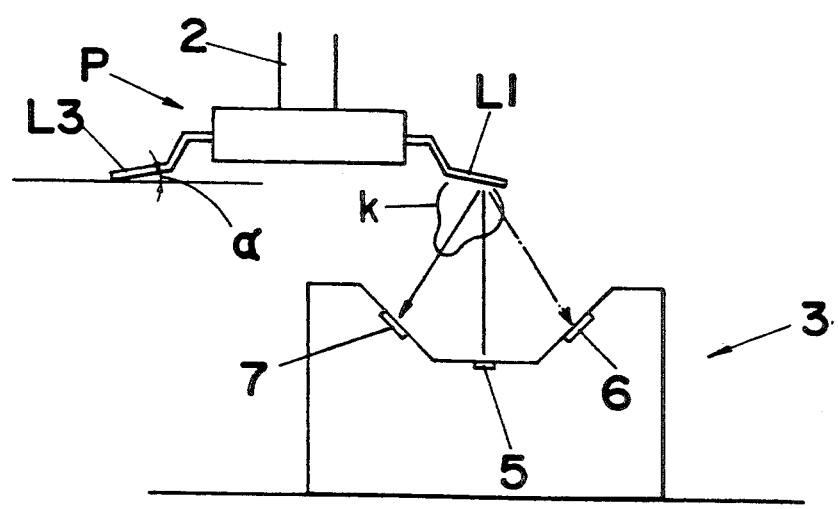

The apparatus of the invention is constructed as described above, and a method of measuring the leads of the electrical component will be described by referring to FIGS. 2 to 4.

The pick and place head 1 sucks the electrical component P. Then, the pick and place head 1 is moved over the measuring apparatus 3 on the way of placing the electrical component P on a printed circuit board, and positions the leads L1 projected from one side a of the molding M above the measuring apparatus 3 (see solid lines in FIG. 4). Then, when the pick and place head 1 is moved in a direction X1 in FIG. 4, a laser light is radiated to be swept along the lateral direction of the leads L1, and the reflected lights are detected by the photodetectors 6 and 7. Dotted broken lines in FIG. 4 designate the position of the electrical component P in which the leads L1 are completely radiated to be swept by the laser light from the laser light emitting unit 5. In this case, as shown in FIG. 2, most of the laser light radiated to the leads L1 is reflected to the photodetector 7 side, but since the reflected lights have directionality as indicated by K in FIG. 2, slight reflected lights are also incident to the other photodetector 6. $\alpha$ indicates the inclining angle of the end of the lead L.

As described above, when the measurements of the leads L1 of one side a of the molding M are finished, the pick and place head 1 is moved in a direction Y1. Thus, the laser light is radiated to be swept at the leads L2 of next side b of the electrical component P. The broken lines in FIG. 4 designate the position of the electrical component P in which the leads L2 are completely radiated to be swept by the laser light from the laser light emitting unit 5. FIG. 3 shows the condition wherein the laser light is radiated to the leads L2. In this case, the leads L2 do not have directionality of the inclining direction to the two photodetectors 6 and 7, and hence the two photodetectors 6 and 7 receive equal or substantially equal amounts of the reflected laser lights.

Then, the pick and place head 1 is similarly moved in directions X2 and Y2. Thus, the leads L3 and L4 of the sides c and d of the electrical component P are sequentially radiated to be swept by the laser light to be measured. As described above, according to the apparatus of the invention, it is not necessary to rotate the pick and place head 1, but the leads L1 to L4 of the four sides of the electrical component P can be rapidly measured by moving the pick and place head 1 to a frame mold in the directions X1, Y1, X2 and Y2 to trace out a rectangular locus as shown in FIG. 4. In this apparatus, the positional deviations of the leads in directions X, Y and Z are measured from the sum of the received amounts of the laser lights of the two photodetectors 6 and 7 or by obtaining the sum and then obtaining the average value. Height information such as floating of the leads is measured from one of the measured values of the two photodetectors 6 and 7 or the average value of both the measured values. Thus, when the measured values of the two photodetectors 6 and 7 are obtained, the reliability of the measured value is enhanced as compared with the case of one photodetector. Further, in case of inspecting the presence or absence of the lead, there is an advantage that, if one of the photodetectors 6 and 7 receives the reflected lights of the lead, the presence of the lead can be determined. At least two photodetectors may be provided to be sufficient at both sides of the light emitting unit, but three or more photodetectors may also be provided.

As described above, the present invention provides the apparatus for measuring leads of an electrical component comprising a light emitting unit for radiating a laser light from below toward the leads projected from a molding of the electrical component sucked to a nozzle of a pick and place head, and first and second photodetectors disposed at both sides of said light emitting unit for detecting laser lights reflected at the leads. Therefore, the leads projected in many radial directions from the molding of the electrical component can be rapidly and accurately measured.

What is claimed is:

1. A method of measuring leads projecting from sides of a molding body of an electrical component, comprising the steps of:
    positioning a pick and place head having means for holding an electrical component over a measuring apparatus having laser light emitting means and photodetector means;
    causing relative movement in a substantially horizontal plane between said pick and place head and said measuring apparatus in four directions such that a locus of said relative movement has a substantially rectangular shape; and
    during said relative movement in each of said four respective directions, radiating laser light from said laser light emitting means toward leads projecting from a respective side of the molding body of the electrical component and causing laser light reflected from said leads to be received by said photodetector means.

2. A method as in claim 1 wherein said photodetector means includes a first and a second photodetector disposed on opposite sides of said light emitting means, and said method further comprises determining deviations of positions of the leads from desired positions thereof from a sum of light amounts received by said first photodetector and said second photodetector.

3. A method as in claim 1, wherein said photodetector means includes a first and a second photodetector disposed on opposite sides of said laser light emitting means, and said method further comprises determining deviations of positions of the leads from desired positions thereof from an average value of light amounts received by said first phototdetector and said second photodetector.

* * * * *